US011707596B2

(12) United States Patent
Garcia Molina et al.

(10) Patent No.: US 11,707,596 B2
(45) Date of Patent: Jul. 25, 2023

(54) METHOD AND SYSTEM TO DELIVER TIMED AND GROUPED SENSORY STIMULATION

(71) Applicant: KONINKLIJKE PHILIPS N.V., Eindhoven (NL)

(72) Inventors: Gary Nelson Garcia Molina, Madison, WI (US); Jesse Salazar, Gibsonia, PA (US); Surya Subrahmanya Sreeram Vissapragada Venkata Satya, Monroeville, PA (US); Antonio Aquino, Harrison City, PA (US); Birpal Singh Sachdev, Delmont, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 530 days.

(21) Appl. No.: 16/832,549

(22) Filed: Mar. 27, 2020

(65) Prior Publication Data
US 2020/0306495 A1 Oct. 1, 2020

Related U.S. Application Data

(60) Provisional application No. 62/825,119, filed on Mar. 28, 2019.

(51) Int. Cl.
*A61M 21/02* (2006.01)
*A61B 5/00* (2006.01)
(Continued)

(52) U.S. Cl.
CPC .......... *A61M 21/02* (2013.01); *A61B 5/4812* (2013.01); *G16H 10/60* (2018.01); *G16H 40/60* (2018.01);
(Continued)

(58) Field of Classification Search
CPC .............................. A61M 21/02; A61B 5/4812
See application file for complete search history.

(56) References Cited

U.S. PATENT DOCUMENTS

| 2016/0220783 | A1* | 8/2016 | Garcia Molina | .... A61B 5/4836 |
| 2017/0340854 | A1* | 11/2017 | Geerlings | ............ A61B 5/4812 |
| 2017/0361060 | A1* | 12/2017 | Garcia Molina | ..... A61M 21/02 |

FOREIGN PATENT DOCUMENTS

| EP | 3229662 A1 | 10/2017 |
| WO | 2014/170781 A1 | 10/2014 |

(Continued)

OTHER PUBLICATIONS

H.-V. V Ngo, T. Martinetz, J. Born, and M. Molle, "Auditory Closed-Loop Stimulation of the Sleep Slow Oscillation Enhances Memory," Neuron, vol. 78, No. May, pp. 1-9, 2013.

(Continued)

*Primary Examiner* — Kaylee R Wilson (57) ABSTRACT

A system for delivering sensory stimulation comprises a sensor configured to measure brain activity information of a patient during a sleep session; a sensory stimulator configured to deliver sensory simulation to the patient during the sleep session; and a computer system. One or more physical processors are programmed with computer program instructions which, when executed cause the computer system to: determine a first stimulation profile, a second stimulation profile, or a combination stimulation profile thereof based on obtained sleep cycle information and/or obtained cognitive domain information; and provide input to the sensory stimulator based on the determined stimulation profile, the provided input causing the sensory stimulator to deliver the sensory simulations to the patient based on the determined stimulation profile during the detected slow wave sleep in the patient.

10 Claims, 6 Drawing Sheets

(51) Int. Cl.
*G16H 10/60* (2018.01)
*G16H 40/60* (2018.01)
*A61M 21/00* (2006.01)
*A61B 5/369* (2021.01)

(52) U.S. Cl.
CPC ...... *A61B 5/369* (2021.01); *A61M 2021/0016* (2013.01); *A61M 2021/0022* (2013.01); *A61M 2021/0027* (2013.01); *A61M 2021/0044* (2013.01); *A61M 2021/0055* (2013.01); *A61M 2230/10* (2013.01)

(56) References Cited

FOREIGN PATENT DOCUMENTS

| WO | 2015/118415 A1 | 8/2015 |
|---|---|---|
| WO | 2016/083929 A1 | 6/2016 |
| WO | 2016092515 A1 | 6/2016 |

OTHER PUBLICATIONS

L. Besedovsky, H.-V. V Ngo, S. Dimitrov, C. Gassenmaier, R. Lehmann, and J. Born, "Auditory closed-loop stimulation of EEG slow oscillations strengthens sleep and signs of its immune-supportive function," Nat. Commun., vol. 8, No. 1, p. 1984, 2017.

N. A. Papalambros, G. Santostasi, R. G. Malkani, R. Braun, S. Weintraub, K. A. Paller, and P. C. Zee, "Acoustic enhancement of sleep slow oscillations and concomitant memory improvement in older adults," Front. Hum. Neurosci., vol. 11, No. March, pp. 1-14, 2017.

G. Santostasi, R. Malkani, B. Riedner, M. Bellesi, G. Tononi, K. A. Paller, and P. C. Zee, "Phase-locked loop for precisely timed acoustic stimulation during sleep," J. Neurosci. Methods, pp. 1-14, 2015.

M. M. Leminen, J. Virkkala, E. Saure, T. Paajanen, P. C. Zee, and G. Santostasi, "Enhanced Memory Consolidation via Automatic Sound Stimulation During Non-REM Sleep," Sleep, vol. 40, No. 3, pp. 1-10, 2017.

C. Diep, S. Ftouni, S. Drummond, and C. Anderson, "Enhancing Slow Wave Activity via an Automated Phase Locked Acoustic Stimulation Sleep," in Sleep 2017, 31st Annual Meeting of the Associated Professional Sleep Societies (APSS), 2017, p. A301.

M. Bellesi, B. Riedner, G. Garcia-Molina, C. Cirelli, and G. Tononi, "Enhancement of sleep slow waves: underlying mechanisms and practical consequences," Front. Syst. Neurosci., vol. 8, No. October, pp. 1-17, Oct. 2014.

G. Tononi and C. Cirelli, "Sleep and the price of plasticity: from synaptic and cellular homeostasis to memory consolidation and integration.," Neuron, vol. 81, No. 1, pp. 12-34, Jan. 2014.

International Search Report and Written Opinion dated Jun. 9, 2020 for International Application No. PCT/EP2020/058160 Filed Mar. 24, 2020.

\* cited by examiner

METHOD AND SYSTEM TO DELIVER TIMED AND GROUPED SENSORY STIMULATION

CROSS-REFERENCE TO PRIOR APPLICATIONS

This application claims the benefit of U.S. Provisional Application No. 62/825,119, filed on 28 Mar. 2019. This application is hereby incorporated by reference herein.

BACKGROUND

1. Field

The present disclosure pertains to a method and a system for delivering sensory stimulation to a patient, specifically, a method and a system to deliver arbitrarily timed and grouped stimulations to enhance slow-wave sleep of the patient.

2. Description of the Related Art

Sleep is a reversible state of disconnection from the external environment, characterized by quiescence and reduced vigilance. The state of the brain and body are not uniform throughout a complete night of sleep, a fact that many believe means that sleep has multiple purposes.

Systems for monitoring sleep are known. Known systems detect sleep stages in a subject during a sleep session. The American Academy of Sleep Medicine (AASM) identifies sleep to be composed out of two distinct types: Rapid-Eye Movement (REM) Sleep and Non-Rapid Eye Movement (NREM) Sleep. It further identifies three stages of NREM sleep, called NREM1, NREM2 and NREM3, with 1 being the lightest NREM sleep and 3 being the deepest NREM sleep. Deeper NREM sleep is associated with larger quantities of slow wave activity (SWA) in the EEG (electroencephalogram). The detected sleep stages include stages that correspond to slow wave sleep. Typically, slow wave sleep is detected based on fixed slow wave detection parameters.

Over the last decade, it has been shown in multiple studies that the use of auditory/sensory stimulation during sleep can enhance sleep slow waves, both in size as well as quantity. Early results indicate that participants undergoing such stimulation feel they sleep better and have better cognitive capacity (for example, they perform better on memory puzzles after the stimulation). In fact, recent research evidence has shown that auditory/sensory stimulation appropriately applied during sleep can enhance sleep slow waves which brings cognitive benefits, promote boosting of sleep restoration, and even strengthen immunologic function. The stimulation is usually delivered in the form of short tones (tens of milliseconds long) timed to specific slow-wave phases.

The stimulation may not happen when subjects are not sleeping deeply enough. If subjects are still awake, studies show that people will take longer to fall asleep. Other experiments show that if the person is not sleeping deep enough, the audio will wake them up (e.g., by causing a cortical arousal). This is why in the current solution the auditory stimulation is limited to NREM3, the deepest sleep stage, thereby preventing sensory stimulation when the user is vigilant enough to hear the sound.

Together with sleep spindles, sleep slow-waves are defining events of the Non-Rapid Eye Movement (NREM) sleep. Sleep slow-waves are believed to mediate the restorative value of sleep by favoring synaptic renormalization during sleep.

Figure 1:
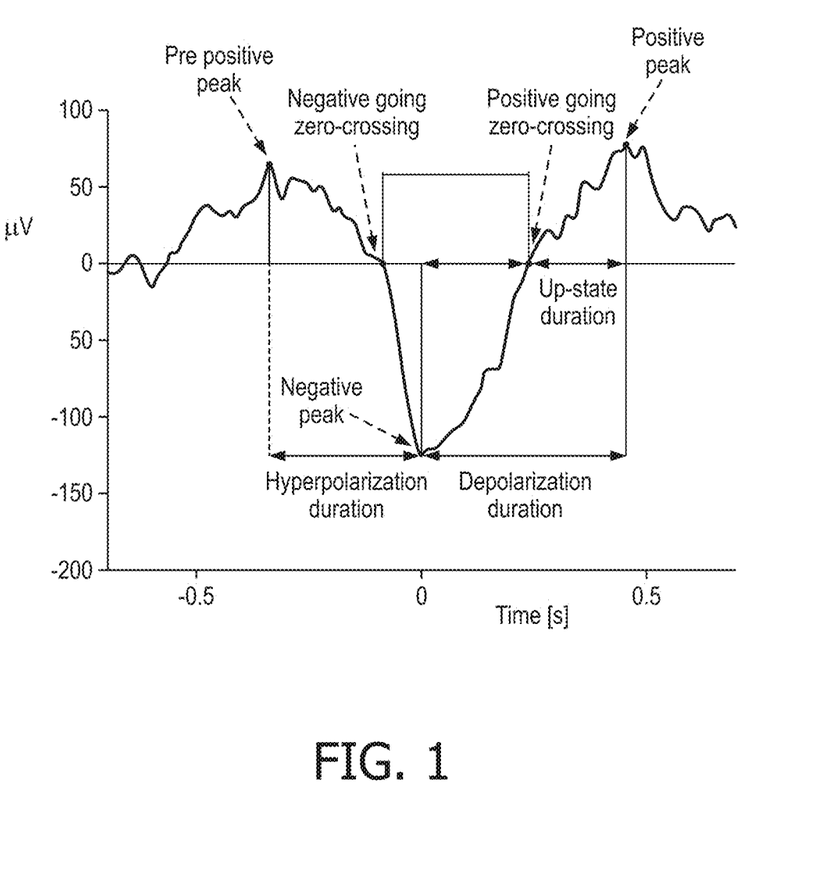
FIG. 1 shows an exemplary graphical representation showing reference points and durations in an exemplary sleep slow-wave.

Sleep slow-waves can be visualized in the electroencephalogram (EEG) during the NREM sleep and particularly in deep (or stage 3, N3) sleep. Relevant reference points and interval durations are shown in FIG. 1. Sleep slow-waves reveal two phases of neural activity during the NREM sleep: 1) hyperpolarization (defined between the pre positive peak and the negative peak) where neurons stop firing and 2) depolarization (defined between the negative peak and the positive peak) where neurons resume firing. The approximate sleep slow-wave duration (interval between the two-positive peaks) is one second.

Referring to FIG. 1, for sleep slow-wave enhancement, auditory or sensory stimulation should fall in the slow-wave up-state or interval between the positive going zero-crossing and the positive peak. The precise detection of sleep slow-waves in real-time is described in the International Patent Application No. WO. 2016092515 A1, "System and method for adjusting slow wave detection criteria."

literature proposes several strategies to adjust the timing of the sensory stimulation. The timing and grouping of the sensory stimulation can be characterized by considering blocks of sensory stimulation with a given number of tones with a fixed or variable inter-tone interval. The interval between blocks is referred to as inter-block interval.

While different types of benefits are reported in the literature, although the most common one appears to be enhanced memory consolidation. Another common element in the literature is that the most effective time to stimulate corresponds to the sleep slow-wa.ve up-state.

This is a relatively young field of research where flexibility in the stimulation timing strategy is important. Tone timing (i.e., phase with respect to slow waves) and grouping (number of tones within an "ON" time period followed by an "OFF" time period) appear to be tightly linked to the effect of the stimulation. Multiple timing-grouping variants are reported in literature with differentiated effects. To enable efficient exploration of different timing choices, flexible stimuli delivery systems are needed.

SUMMARY

Accordingly, it is an object of one or more embodiments of the present patent application to provide a system for delivering sensory stimulation. The system comprises: a sensor configured to measure brain activity information of a patient during a sleep session; a sensory stimulator configured to deliver sensory simulation to the patient during the sleep session; and a computer system that comprises one or more physical processors operatively connected with the sensor and the sensory stimulator. The one or more physical processors are programmed with computer program instructions which, when executed cause the computer system to: obtain sleep cycle information of the patient and cognitive domain information of the patient; detect slow wave sleep in the patient based on the brain activity information of the patient during the sleep session from the sensor; determine a first stimulation profile, a second stimulation profile, or a combination stimulation profile thereof based on the obtained sleep cycle information and the obtained cognitive domain information; and provide input to the sensory stimulator based on the determined stimulation profile, the provided input causing the sensory stimulator to deliver the sensory simulation to the patient based on the determined stimulation profile during the detected slow wave sleep in the patient.

It is yet another aspect of one or more embodiments of the present patent application to provide a method for delivering sensory stimulation. The method is implemented by a computer system comprising one or more physical processors executing computer program instructions that, when executed, perform the method. The method comprises obtaining sleep cycle information of a patient and/or cognitive domain information of the patient; detect slow wave sleep in the patient based on brain activity information of the patient during the sleep session from a sensor; determining, using the computer system, a first stimulation profile, a second stimulation profile, or a combination stimulation profile thereof based on the obtained sleep cycle information and/or the obtained cognitive domain information; and providing, using the computer system, input to a sensory stimulator based on the determined stimulation profile, the provided input causing the sensory stimulator to deliver the sensory simulations to the patient based on the determined stimulation profile during the detected slow wave sleep in the patient.

It is yet another aspect of one or more embodiments to provide a system for delivering sensory stimulation. The system comprises a means for measuring brain activity information of a patient during a sleep session; a means for delivering sensory stimulation to the patient during the sleep session, the sensory stimulation having varying stimulation intensity levels; and a means for executing machine-readable instructions with at least one processor, wherein the machine-readable instructions comprising: obtaining sleep cycle information of a patient and/or cognitive domain information of the patient; detecting slow wave sleep in the patient based on brain activity information of the patient during the sleep session from the means for measuring; determining a first stimulation profile, a second stimulation profile, or a combination stimulation profile thereof based on the obtained sleep cycle information and/or the obtained cognitive domain information; and providing input to the means for delivering based on the determined stimulation profile, the provided input causing the means for delivering to deliver the sensory simulations to the patient based on the determined stimulation profile during the detected slow wave sleep in the patient.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. As used herein, the term "or" means "and/or" unless the context clearly dictates otherwise.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present patent application provides a system 100 for delivering sensory stimulation. System 100 comprises: a sensor 102 configured to measure brain activity information of a patient during a sleep session; a sensory stimulator 104 configured to deliver sensory simulation to the patient during the sleep session; and a computer system 106 that comprises one or more physical processors 108 operatively connected with sensor 102 and sensory stimulator 104. One or more physical processors 108 are programmed with computer program instructions which, when executed cause the computer system 106 to: obtain sleep cycle information of the patient and cognitive domain information of the patient; detect slow wave sleep in the patient based on the brain activity information of the patient during the sleep session from sensor 102; determine a first stimulation profile, a second stimulation profile, or a combination stimulation profile thereof based on the obtained sleep cycle information and the obtained cognitive domain information; and provide input to sensory stimulator 104 based on the determined stimulation profile, the provided input causing sensory stimulator 104 to deliver the sensory simulation to the patient based on the determined stimulation profile during the detected slow wave sleep in the patient.

In some embodiments, an integrated system of the present patent application is configured to deliver arbitrarily timed and clustered tones. In some embodiments, tones can be accurately delivered due to the integrated nature of the system and the capability to detect reference points on an ongoing sleep slow-wave. In some embodiments, specific timing choices are supported by statistics on interval durations between several sleep slow-wave reference points. In some embodiments, sleep slow-wave reference points include all the features (i.e., reference points and durations in an exemplary sleep slow-wave) shown in FIG. 1. In some embodiments, system 100 of the present patent application provides new optimized stimulation timing strategies as described in detail below. In some embodiments, in this patent application, patient may be interchangeably referred to as a consumer, a user, an individual or a subject.

In some embodiments, sensor 102 is configured to measure brain activity information of the patient during the sleep session. In some embodiments, sensor 102 may be referred to as EEG sensing unit. In some embodiments, the EEG sensing unit/sensor 102 is configured to continuously monitor EEG throughout the sleep session of the patient via one or more EEG sensors 102 attached to the patient's head. In some embodiment, signals from the one or more EEG sensors 102 are fed into a signal analysis/processing unit 106.

In some embodiments, information related to brain activity of the patient may include and/or be indicative of slow wave activity (SWA) in the patient (e.g., slow waves, sleep spindles, K-complexes, etc.), sleep pressure in the patient, a sleep stage of the patient, and/or other characteristics of the patient. In some embodiments, sensor 102 may comprise one or more sensors that generate output signals conveying such information directly. For example, sensor 102 may include electrodes configured to detect electrical activity resulting from current flows within the brain of the patient. In some embodiments, sensor 102 may comprise one or more sensors that generate output signals conveying information related to brain activity during sleep of the patient indirectly. For example, one or more sensors 102 may generate an output based on a heart rate of the patient (e.g., sensor 102 may be a heart rate sensor), movement of the patient (e.g., sensor 102 may include an accelerometer such that sleep may be analyzed using actigraphy signals), respiration of the patient, skin conductance, temperature, and/or other characteristics of the patient. In some embodiments, a portion of sensor 102 is formed by the conductive material described above that contacts the ear of the patient.

As another example, the information related to the brain activity of the patient may be obtained from one or more monitoring devices (e.g., EEG monitoring device, or other brain activity monitoring devices). In some embodiments, one or more monitoring devices and associated sensors 102 may be configured to monitor the brain activity of patient. These monitoring devices may include one or more sensors 102. Sensor 102 may, for instance, be configured to obtain information related to the brain activity of patient.

Figure 2:
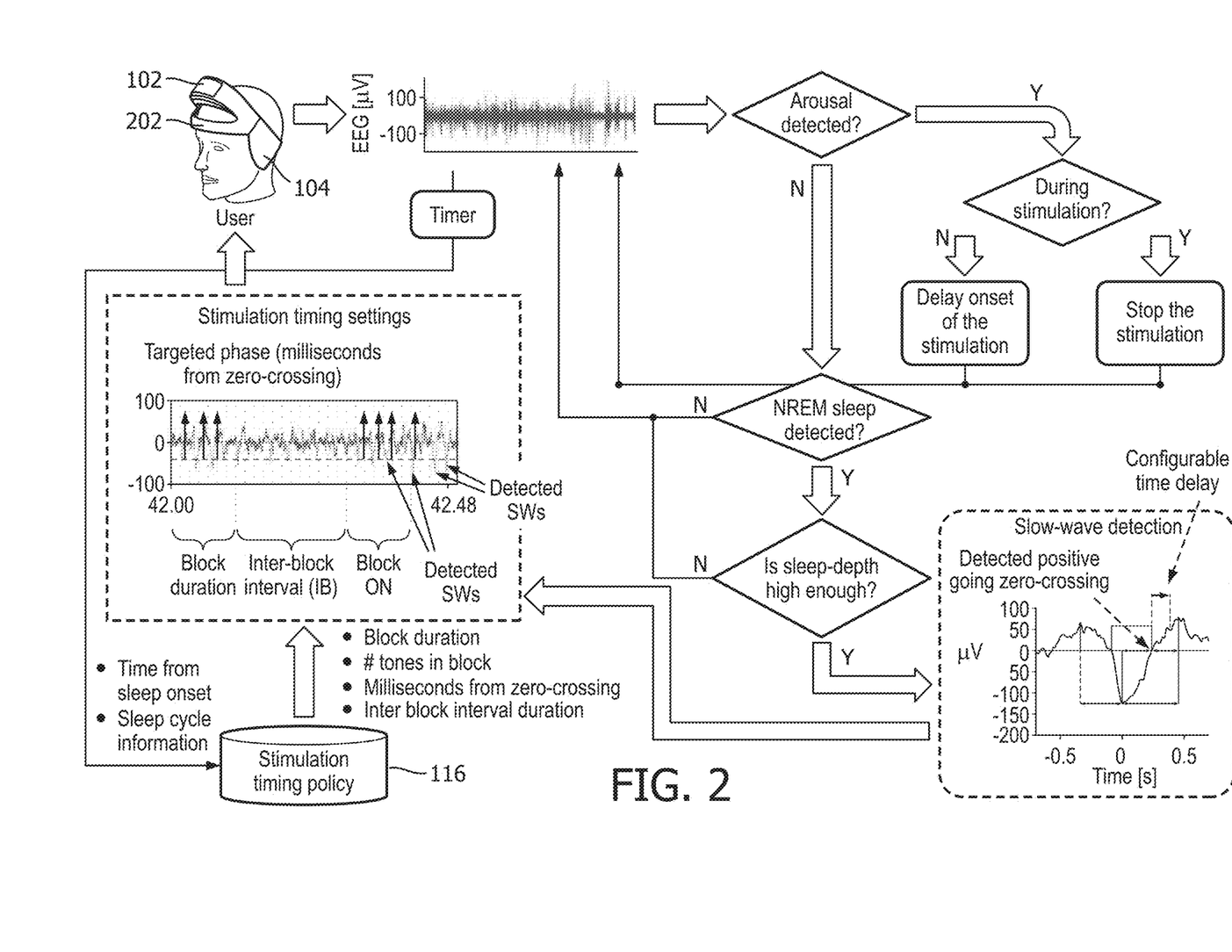
FIG. 2 shows an exemplary system and method to deliver arbitrarily timed and grouped auditory stimulation to enhance slow-wave sleep in accordance with an embodiment of the present patent application.
Figure 3:
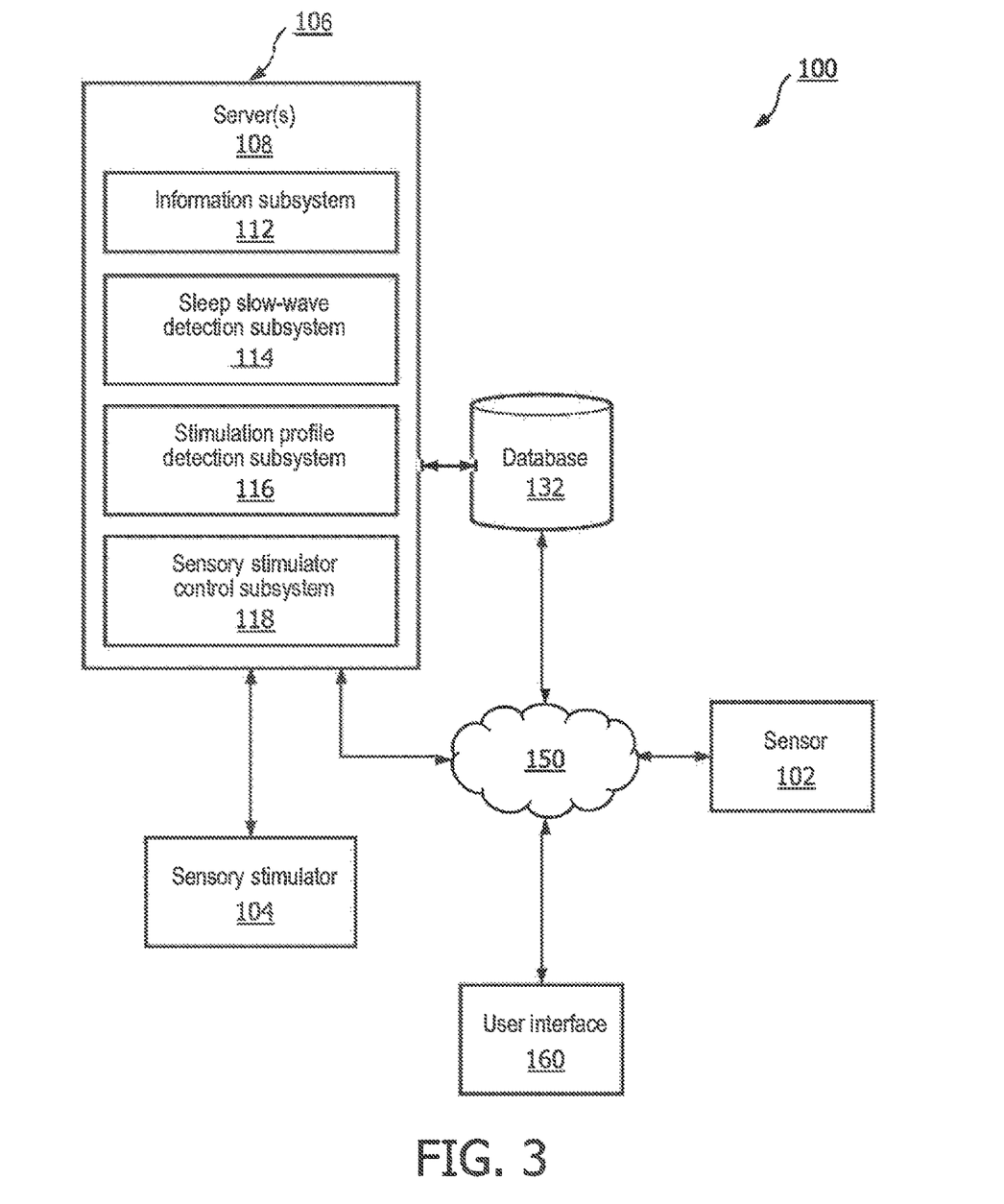
FIG. 3 shows an exemplary system for delivering sensory stimulation in accordance with an embodiment of the present patent application.
Figure 4:
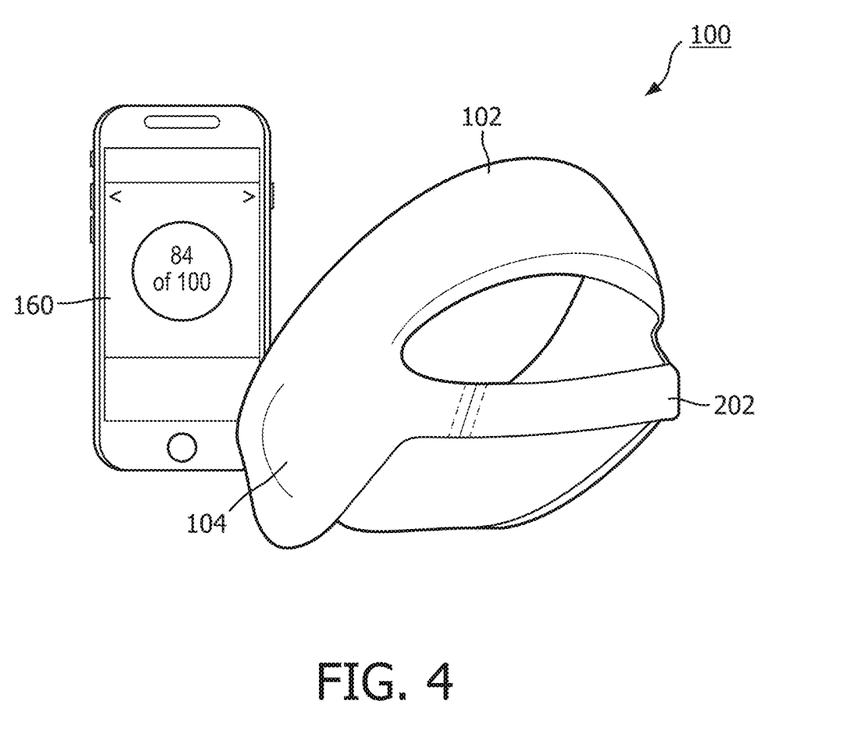
FIG. 4 shows an exemplary system for measuring brain activity information of the patient during a sleep session and delivering sensory simulation to the patient during the sleep session in accordance with an embodiment of the present patent application.

In some embodiments, sensor 102 includes a transmitter for sending signals/information and a receiver for receiving the signals/information. In some embodiments, sensor 102 is configured to communicate wirelessly with computer system 106. As shown in FIGS. 2-4, in some embodiments, sensor 102 is configured to be operatively connected with computer system 106 and/or one or more physical processors 108 of computer system 106. In some embodiments, sensor 102 is configured to communicate with sensory stimulator 104. In some embodiments, sensor 102 is in communication with a database 132. In some embodiments, the information related to the brain activity of the patient may be obtained from the database 132 that is being updated in real-time by sensor 102.

In one scenario, a monitoring device may obtain information (e.g., based on information from sensor 102), and provide information to computer system 106 (e.g., comprising server 108) over a network (e.g., network 150) for processing. In another scenario, upon obtaining the information, the monitoring device may process the obtained information, and provide processed information to computer system 106 over a network (e.g., network 150). In yet another scenario, the monitoring device may automatically provide information (e.g., obtained or processed) to computer system 106 (e.g., comprising server 108).

In some embodiments, sensor 102 is configured to generate output signals conveying information related to brain activity of the patient and/or other information. Sensor 102 is configured to generate output signals in an ongoing manner during the sleep session of the patient, at regular intervals during the sleep session, and/or at other times. In some embodiments, the brain activity of the patient may correspond to a current sleep stage, SWA in the patient, and/or other characteristics of the patient. In some embodiments, the brain activity of the patient may be associated with rapid eye movement (REM) sleep, non-rapid eye movement (NREM) sleep, and/or other sleep. In some embodiments, sleep stages of the patient may include one or more of NREM stage N1, stage N2, or stage N3 sleep, REM sleep, and/or other sleep stages. In some embodiments, N1 corresponds to a light sleep state and N3 corresponds to a deep sleep state. In some embodiments, NREM stage 3 or stage 2 sleep may be slow wave (e.g., deep) sleep. In some embodiments, sensor 102 may comprise one or more sensors that measure such parameters directly and/or indirectly. For example, sensor 102 may include electrodes configured to detect electrical activity along the scalp of the patient resulting from current flows within the brain of the patient. In some embodiments, one or more sensors 102 are EEG electrodes, and/or other sensors. In some embodiments, an EEG exhibits changes throughout a sleep session of the patient. In some embodiments, a prominent change in the EEG delta power (also known as slow wave activity (SWA)) is typically visible, for example.

Although, in some embodiments, sensor 102 may be positioned at a single location near the patient, this is not intended to be limiting. Sensor 102 may include one or more sensors disposed in a plurality of locations, such as for example, coupled in a removable manner with the skin of the patient, coupled in a removable manner with clothing of the patient, worn by the patient (e.g., as a headband 202 (as shown in FIGS. 2 and 4), a wristband, a hood worn by the patient etc.), and/or in other locations. For example, sensor 102 may be removably coupled with the skin of the patient via a sticker and/or other coupling mechanisms. In some embodiments, sensor 102 is placed slightly below the mastoid of the patient near major arteries of the patient. In some embodiments, sensor 102 are attached to the patient with stickers. In some embodiments, sensor 102 is either applied to directly to a patient's head or integrated into some kind of cap to be worn by the patient.

In some embodiments, sensory stimulator 104 is also referred to as an actuator or a stimulation actuator. In some embodiments, sensory stimulator 104 is configured to receive information from computer system 106 and to generate and provide sensory stimulation to the patient based on the received information. In some embodiments, sensory stimulator 104 is configured to stop, continue/resume, adjust, or start sensory stimulation provided to the patient based on the information received from computer system 106.

In some embodiments, the received information from computer system 106 may include determined sensory stimulation profile and/or the detected sleep slow-wave information. In some embodiments, sensory stimulator 104 is configured to generate and provide sensory stimulation based on the determined sensory stimulation profile and/or the detected sleep slow-wave information. In some embodiments, sensory stimulator 104 is configured to adjust the stimulation intensity of sensory stimulation provided to the patient based on the information received from computer system 106.

In some embodiments, sensory stimulator 104 is configured to provide sensory stimulation to the patient during the least arousable state of the patient based on the received information related to the brain activity of the patient and the determined stimulation profile.

In some embodiments, sensory stimulator 104 is configured to provide sensory stimulation to the patient prior to a sleep session, during a sleep session, after a sleep session, and/or at other times. In some embodiments, sensory stimulator 104 is configured to provide sensory stimulation to the patient without causing arousals during sleep. In some embodiments, for example, sensory stimulator 104 may be configured to provide sensory stimulation to the patient during slow wave sleep in the sleep session. In some embodiments, sensory stimulator 104 may be configured to provide sensory stimulation to the patient to induce and/or adjust slow wave activity (SWA) in the patient. In some embodiments, sleep slow waves are associated with slow wave activity (SWA) in the patient during the sleep session. In some embodiments, sensory stimulator 104 is configured such that inducing and/or adjusting SWA includes inducing, increasing, and/or enhancing sleep slow waves in the patient.

In some embodiments, sensory stimulator 104 may be configured to induce, increase, and/or enhance sleep slow waves through non-invasive brain stimulation and/or other methods. In some embodiments, sensory stimulator 104 may be configured to induce, increase, and/or enhance sleep slow waves through non-invasive brain stimulation using sensory stimulation.

In some embodiments, system 100 is configured to be applied for various types of sensory stimulation, including auditory, visual and somatosensory stimuli. In some embodiments, the sensory stimulation may include different types of sensory stimulations. In some embodiments, the sensory stimulation is selected from the group consisting of olfactory stimulation, somatosensory stimulation, auditory stimulation, visual stimulation, touch stimulation, taste stimulation, haptic stimulation, peripheral stimulation, magnetic stimulation and electrical stimulation. In some embodiments, the sensory stimulation is a peripheral stimulation (magnetic or electrical stimulation). In some embodiments, the sensory stimulation may include smells, tones, odors, sounds, visual stimulation (e.g., lights flashed on open and/or closed eyes), touches, tastes, haptic (e.g., vibrations or non-contact haptic) stimulation, and/or other sensory stimulations. In some embodiments, for example, acoustic tones may be provided to the patient to induce, increase, and/or enhance sleep slow waves. In some embodiments, examples of sensory stimulator 104 may include one or more of a music player, a tone generator, a collection of electrodes on the scalp of the patient, a unit to deliver vibratory stimulation (also known as somato-sensory stimulation), a coil generating a magnetic field to directly stimulate the brain's cortex, light generators, a fragrance dispenser, and/or other sensory stimulators.

In some embodiments, sensory stimulator 104 includes wireless audio device and one or more audio speakers. In some embodiments, headband 202 (as shown in FIGS. 2 and 4) may be worn by the patient. In some embodiments, headband 202 includes the wireless audio device and the one or more audio speakers. In some embodiments, the one or more audio speakers may be located in and/or near the ears of the patient.

In some embodiments, interchangeable earbud attachments in a range of sizes (e.g., small (S), medium (M), and large (L) are configured to removably couple with a housing of ear insert such that the patient may find an interchangeable earbud attachment that is most comfortable and attach it to the housing. In some embodiments, earbud attachments are formed from the conductive materials such that earbud attachments form a portion of sensor 102.

In some embodiments, the housing includes electronic components that form a portion of sensor 102, sensory stimulator 104, and/or other components of system 100. In some embodiments, sensory stimulator 104, sensor 102 are formed integrally with the ear insert such that the ear insert, sensory stimulators 104, and sensor 102 appear to form a single unified physical object that is comfortable for the patient to insert and remove from his or her ears. In some embodiments, the ear insert is custom formed based on three dimensional data representative of the ear of the patient, a physical mold/model of the ear of the patient, and/or other information. Whether a custom ear insert is fabricated directly based on the three dimensional data or fabricated from a mold or other components formed based on the three dimensional data, the ear insert may be customized based on the three dimensional data to fill the ear canal of the patient and much of the outer ear of the patient without protruding from the head of the patient so as to enable comfort during sleep and/or other activities (e.g., maximizing the surface area ear insert that is in contact with the ear of the patient without hindering comfort). In some embodiments, the ear insert may be customized to include a small canal built into the ear insert (e.g., with an approximate diameter of about 2-3 mm) to facilitate hearing ambient sounds (e.g., during sleep and/or while awake). In some embodiments, the ear insert may be customized such than an area of the ear insert under the tragus of the patient is smoothed to allow the tragus room for lying against the earpiece should the patient elect to sleep on their side, for example.

In some embodiments, the housing and the earbud attachments form correspond clamping or other engagement surfaces configured to removably couple with each other. In some embodiments, engagement surface on the housing includes a conductive surface such that electrical signals passing through the earbud attachments are received by the housing. In some embodiments, the housing may include one or more features (e.g., a hook that wraps around the ear of the patient) to enhance coupling with the ear of the patient. In some embodiments, the ear insert are made at three different levels of material elasticity (e.g., very soft, soft, and hard).

In some embodiments, system 100 includes computer system 106 that comprises one or more physical processors 108 operatively connected with sensor 102 and sensory stimulator 104. In some embodiments, one or more physical processors 108 are programmed with computer program instructions which, when executed cause computer system 106 to perform various functions.

As shown in FIG. 3, system 100 may comprise server 108 (or multiple servers 108). In some embodiments, server 108 includes one or more physical/hardware processors 108. In FIG. 3, database 132 is shown as a separate entity, but, in some embodiments, database 132 could be part of computer system 106. As will be clear from the discussions above and below, in some embodiments, system 100 includes computer system 106 that has one or more physical/hardware processors 108 programmed with computer program/machine readable instructions that, when executed cause computer system 106 to obtain information/data from sensor 102. In some embodiments, computer system 106 may also be referred to as means 106 for executing machine readable instructions with at least one hardware processor 108.

In some embodiments, server 108 comprises information subsystem 112, sleep slow-wave detection subsystem 114, stimulation profile determination subsystem 116, sensory stimulator control subsystem 118 or other components or subsystems. In some embodiments, information subsystem 112, sleep slow-wave detection subsystem 114, stimulation profile determination subsystem 116, sensory stimulator control subsystem 118 or other components or subsystems together may be referred to as signal processing or signal analysis device/unit.

In some embodiments, information subsystem 112 is configured to receive or obtain the brain activity information of the patient from sensor 102. In some embodiments, information subsystem 112 is configured to further process the received or obtained brain activity information. In some embodiments, information subsystem 112 comprises a brain activity signal feature extraction unit that is configured to extract the brain activity features from the signals, data or information provided by sensor 102. In some embodiments, information subsystem 112 is optional and the brain activity information of the patient from sensor 102 may be directly received or obtained by sleep slow-wave detection subsystem 114. In such an embodiment, sleep slow-wave detection subsystem 114 comprises a brain activity feature extraction unit that is configured to extract the brain activity features from the signals, data or information provided by sensor 102.

In some embodiments, information subsystem 112 is configured to receive or obtain sleep cycle information. In some embodiments, the sleep cycle information includes time from sleep onset, biological signals, sleep spindle density or count thereof, sleep patterns, sleep stages, number of prior sleep cycles, and/or a measure of quality of a user's sleep. In some embodiments, system 100 is configured to obtain or receive the sleep cycle information from the patient. In some embodiments, the sleep cycle information is provided by sensor 102. In some embodiments, sleep cycle information are input by the patient (or caregiver) into computer system 106 using user interface 160. In some embodiments, computer system 106 may include sleep cycle information subsystem for further processing this information.

In some embodiments, inputs for stimulation timing policy module/stimulation profile detection subsystem 116 include time from sleep onset and potentially information on the sleep cycle. This enables system 100 to apply different stimulation strategies depending on the sleep cycle or block count. This is useful for comparing different stimulation strategies within the same sleep session (i.e., removing the confounding effect of night-to-night variability).

In some embodiments, information subsystem 112 is configured to receive or obtain cognitive domain information. In some embodiments, the cognitive domain information includes vigilance, working memory (verbal and non-verbal), memory consolidation, endocrine activity level (e.g., aldosterone levels or cortisol levels), motors skills, executive function, visual spatial skills, verbal fluency, attention, information processing, emotion processing, fluid intelligence etc. In some embodiments, aldosterone or cortisol levels are not cognitive parameters but rather reflect endocrine balance or endocrine activity level. In some embodiments, system 100 is configured to obtain or receive the cognitive domain information from the patient. In some embodiments, the cognitive domain information are input by the patient (or caregiver) into computer system 106 using user interface 160. In some embodiments, computer system 106 may include cognitive domain information subsystem for further processing this information.

In some embodiments, sleep slow-wave detection subsystem 114 is configured to extract a characteristic from the signals, data or information obtained from sensor 102 and that is proportional to the brain activity. In some embodiments, sleep slow-wave detection subsystem 114 includes extraction algorithms configured to extract a characteristic from the signals, data or information obtained from sensor 102 and that is proportional to the brain activity. In some embodiments, sleep slow-wave detection subsystem 114 includes machine learning based methods (i.e., that were trained using historical data/information) are configured to extract a characteristic from the signals, data or information obtained from sensor 102 and that is proportional to the brain activity. In some embodiments, sleep slow-wave detection subsystem 114 includes a processing module or a signal processing module.

In some embodiments, on detection of non-rapid eye movement (NREM) sleep (which can be Stage N2 or Stage N3 sleep), a first test considers whether sleep depth (i.e., ratio between the EEG power in the 0.5 to 4 Hz band and the EEG power in the 15 to 30 Hz band) is sufficiently high to deliver the sensory stimulation.

In some embodiments, sleep slow-waves are detected using a slow-wave detection algorithm. In some embodiments, system 100 is configured to use a slow-wave detection algorithm disclosed in International Patent Application Publication WO 2016092515 A1 "System and method for adjusting slow wave detection criteria," which is incorporated herein by reference in its entirety.

In some embodiments, the negative peak and zero-crossings can be detected in real-time by embedded integrated platform. In some embodiments, referring to FIGS. 1 and 5, sleep slow-wave detection subsystem 114 is configured to detect positive going zero-crossing (e.g., in the up-state duration, in the depolarization duration).

Figure 5:
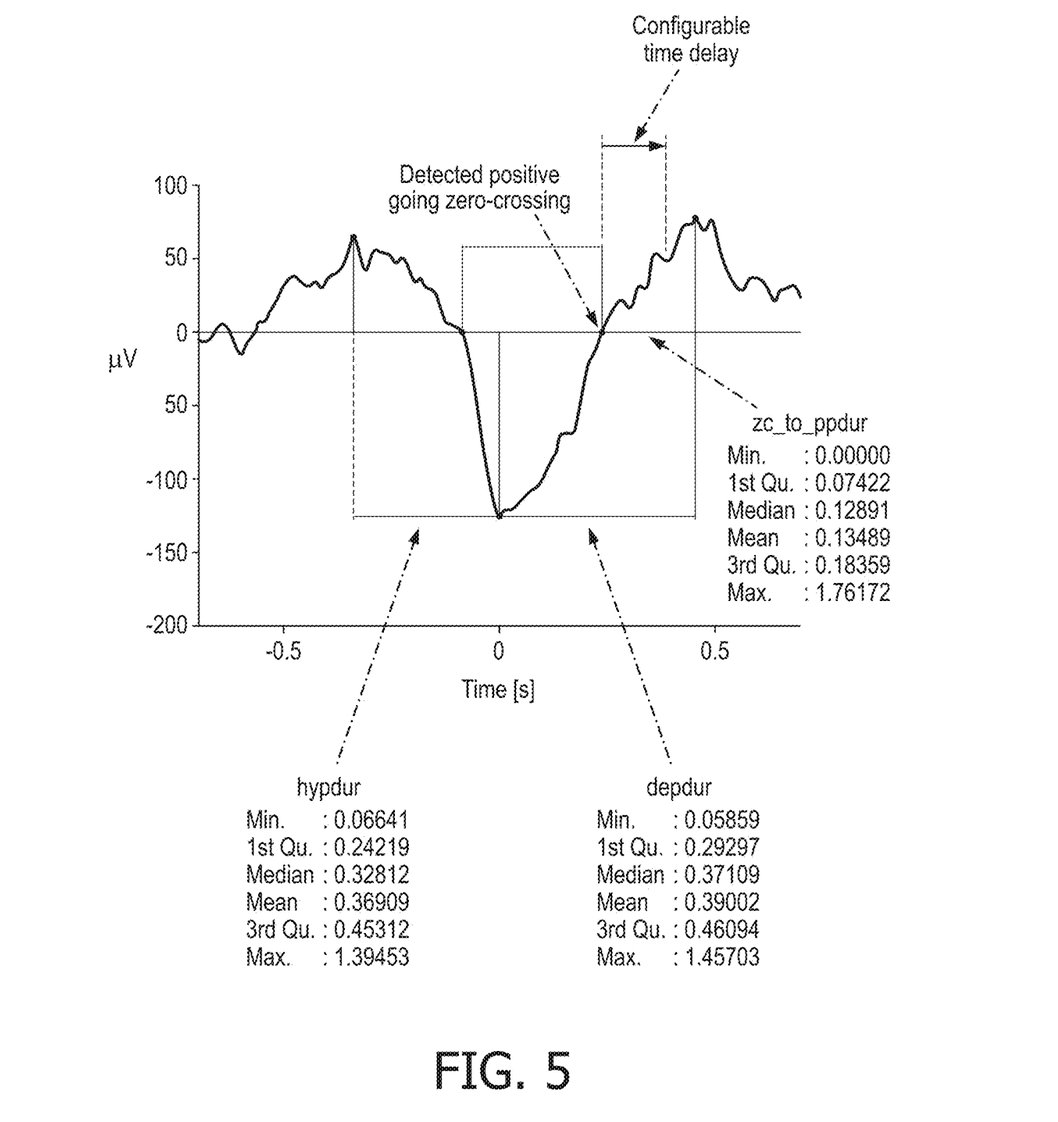
FIG. 5 shows an exemplary graphical representation showing statistics on the duration of sleep slow-wave relevant intervals in accordance with an embodiment of the present patent application.

In some embodiments, the integrated nature of system 100 is advantageous as it enables setting the stimulation time with respect to a slow-wave by fixing a delay from the moment the positive going zero crossing is detected. In some embodiments, as shown in FIG. 5, to target the slow-wave up-state, the delay can be set to 80 milliseconds (i.e., as 74 milliseconds represents the $25^{th}$ percentile of the up-state distribution). In some embodiments, the delay may include other time periods. In some embodiments, real-time detection of slow-wave reference points removes the need of prediction (i.e., which inevitably introduces errors) of slow-wave timing or timing the stimulation with respect to a negative peak.

In some embodiments, stimulation timing policy module/stimulation profile detection subsystem 116 is configured to determine a first stimulation profile, a second stimulation profile, or a combination stimulation profile thereof based on the obtained sleep cycle information and the obtained cognitive domain information.

In some embodiments, each of the first, second and combination stimulation profiles, among other things, may include information that is selected from the group consisting of stimulation timing when the sensory stimulation is delivered to the patient, duration of a sensory stimulation block (i.e., block duration), number of tones in the sensory stimulation block (i.e., number of consecutive stimulations to deliver), configurable in-phase time delay (e.g., milliseconds from) from a positive going zero-crossing (or the negative peak), duration of an inter-block interval (IBI), an inter-tone interval (ITI), duration of continuous detected deep-sleep before the stimulation can initiate, number of sleep slow waves to skip between sensory stimulation blocks, a duration to wait after detecting suitable sensory stimulation conditions and before beginning the sensory stimulation blocks, a duration to wait after detecting arousal conditions and before beginning the sensory stimulation blocks, whether to synchronize a sensory stimulation block its first sensory stimulation with an up-state of a first subsequent slow-wave after the duration of the inter-block interval (IBI) is satisfied (i.e., each block of stimulation should synchronize its first stimulation with the up-state of a slow-wave after the inter-block interval (IBI) duration is satisfied), a time delay after deep sleep (the slow wave sleep) is detected and before starting the sensory stimulation or sensory stimulation blocks (e.g., wait at least 3 minutes in detected deep sleep before starting the stimulation), etc.

In some embodiments, tone timing (i.e., phase with respect to slow waves) and grouping (number of tones within an "ON" time period followed by an "OFF" time period) appear to be tightly linked to the effect of the sensory stimulation being delivered. In some embodiments, the timing and grouping of the sensory stimulation can be characterized by considering blocks of sensory stimulation with a given number of tones with a fixed or variable inter-tone interval. In some embodiments, a tone is delivered for every detected slow wave. In some embodiments, sensory stimulator 104 is configured to deliver sensory stimulation to the patient at a fixed inter-tone stimulation interval (ITI). In some embodiments, the fixed inter-tone stimulation interval may be 1 second, and/or other predetermined intervals. In some embodiments, the interval between blocks is referred to as inter-block (IBI) interval.

In some embodiments, the determined stimulation profile includes a fixed ITI, block-based stimulation, or a hybrid thereof. In some embodiments, block stimulation profile typically renders the sensory stimulation with a fixed periodicity.

In some embodiments, during the time-based IBI, the blocks of tones are consistently separated by an unchanging amount of time. In some embodiments, during the count-based IBI, the blocks of tones are consistently separated by a slow-wave count. In some embodiments, during the sync first block, in-sync first tone of first block, are followed by ITI tones. That is, the first tone is always in-phase, with subsequent tones out of phase. In some embodiments, during the sync every block, in-sync first tone of every block, are followed by ITI tones. That is, the first tone is always in-phase.

In some embodiments, during the arousal-Delay, noise is added to an otherwise steady II-Iz sinusoid pauses stimulation for a consistent amount of time. In some embodiments, during the post-zero crossing delay, when sinusoid waveforms that have the same duration are fed in, negative peaks are at slightly shifted positions. Also, the stimulation occurs after consistent delay, post-zero-cross, rather than with respect to post-negative peak. In some embodiments, when a 0.3 Hz sinusoid waveform is fed in, it is observed that the takes over. In some embodiments, when a 2 Hz sinusoid waveform is fed in, it is observed that every slow-wave is targeted, in-phase.

In some embodiments, referring to FIGS. 2 and 3, stimulation timing policy module/stimulation profile detection subsystem 116 may include configuration rules to set the duration of a block, the number of tones in a block, the duration of the inter-block interval, and the delay in milliseconds from the detection of the positive going zero-crossing.

In some embodiments, stimulation approaches are made possible via the real-time Slow Wave detection methods described in WO 2016092515 A1, rather than relying on manual intervention or a P11 implementation to drive stimulation. In some embodiments, stimulation timing policy module/stimulation profile detection subsystem 116 is configured by parameters defined in three logical groups, enforcing the parameters by use of clock mechanisms provided via enclosing [integrated] embedded system 100.

In some embodiments, the first stimulation profile includes a subset of parameters defining behavior within a stimulation block including an inter-tone interval (ITI) and number to consecutive sensory stimulations to be delivered. In some embodiments, the inter-tone interval (ITI) is to be used in applications where fixed stimulation timing is desired. In some embodiments, continuous or in-block stimulation is provided and the tones are separated from each other by a fixed inter-tone interval (ITI).

In some embodiments, the first stimulation profile also includes a subset of parameters defining behavior between stimulation blocks: including a) a time-based inter-block interval (IBI-Time), or amount of time to pause stimulation after the Block-Count parameter is satisfied, before beginning stimulation again; b) a slow-wave-count inter-block interval (IBI-Count), or number of slow-waves to skip after the Block-Count parameter is satisfied, before beginning stimulation again; c) a flag indicating whether the IBI-Time or IBI-Count (IBI-Mode) parameter is to be used on a given night, or within a given sleep cycle, determined by the enclosing application as needed; and/or d) a sync-each-block flag (Sync-Each-Block), indicating whether each block of stimulation should synchronize its first stimulation with the up-state of a slow-wave (after the inter-block interval, IBI, has been satisfied). In some embodiments, the first stimulation profile also includes a subset of parameters defining behavior that transcends stimulation blocks: a) a Policy delay (Policy-Delay), specifying a duration of time to wait, after detecting suitable stimulation conditions, before beginning stimulation blocks altogether; b) an arousal delay (Arousal-Delay), specifying a duration of time to wait, after detecting arousal conditions, before allowing stimulation blocks to begin, or continue again; and/or c) a sync-first-block flag (Sync-First-Block), indicating whether the very first NREM stimulation block should synchronize its first stimulation with the up-state of the first subsequent slow-wave, independent of the Sync-Each-Block parameter in the previous section.

In some embodiments, the second stimulation profile includes a subset of parameters defining behavior within a stimulation block including an in-phase delay and number to consecutive sensory stimulations to be delivered. In some embodiments, the post-zero-crossing delay (In-Phase-Delay) after which to deliver each sensory stimulation, to be used in applications not covered by the inter-tone interval (ITI).

In some embodiments, the second stimulation profile also includes a subset of parameters defining behavior between stimulation blocks: including a) a time-based inter-block interval (IBI-Time), or amount of time to pause stimulation after the Block-Count parameter is satisfied, before beginning stimulation again; b) a slow-wave-count inter-block interval (IBI-Count), or number of slow-waves to skip after the Block-Count parameter is satisfied, before beginning stimulation again; c) a flag indicating whether the IBI-Time or IBI-Count (IBI-Mode) parameter is to be used on a given night, or within a given sleep cycle, determined by the enclosing application as needed; and/or d) a sync-each-block flag (Sync-Each-Block), indicating whether each block of stimulation should synchronize its first stimulation with the up-state of a slow-wave (after the inter-block interval, IBI, has been satisfied). In some embodiments, the second stimulation profile also includes a subset of parameters defining behavior that transcends stimulation blocks: a) a Policy delay (Policy-Delay), specifying a duration of time to wait, after detecting suitable stimulation conditions, before beginning stimulation blocks altogether; b) an arousal delay (Arousal-Delay), specifying a duration of time to wait, after detecting arousal conditions, before allowing stimulation blocks to begin, or continue again; and/or c) a sync-first-block flag (Sync-First-Block), indicating whether the very first NREM stimulation block should synchronize its first stimulation with the up-state of the first subsequent slow-wave, independent of the Sync-Each-Block parameter in the previous section.

In some embodiments, stimulation timing policy module/stimulation profile detection subsystem 116 is configured to define the following subset of parameters defining behavior within a stimulation block: a) an inter-tone interval (ITI), to be used in applications where fixed stimulation timing is desired; b) the post-zero-crossing delay (In-Phase-Delay) after which to deliver each sensory stimulation, to be used in applications not covered by the inter-tone interval (ITI); c) a flag (Use-ITI) indicating whether the ITI parameter should be utilized, or whether the In-Phase-Delay parameter should be utilized (referred to as in-phase profiles); and/or d) the tones-per-block count (Block-Count), indicating the number of consecutive stimulations to deliver, where "consecutive stimulations" are defined by the ITI flag as either timed opportunities, or consecutive slow-waves (detected via WO 2016092515 A1 or other methods) for which stimulations are delivered (in-phase).

In some embodiments, system 100 integrates the benefits of the in-phase methods and literature discussed above, and the benefits of the ITI methods as well, attempting to achieve a set-point for entrainment while still capitalizing on the in-phase synchronization. In some embodiments, hybrid/combination stimulation strategies are useful for comparison purposes, i.e., to determine the optimal stimulation policy/profile for a given user within the same sleep session. The same sleep session aspect is particularly important as this removes the nigh-to-night variability confounding factor.

In some embodiments, system 100 provides a configuration option for further combining both the ITI, and In-Phase stimulation profiles. In some embodiments, a single additional parameter indicates whether or not stimulation timing policy module/stimulation profile detection subsystem 116 deploys a "Hybrid-ITI" stimulation profile, achieved by the following: (a) utilize all parameters in the embodiment, but replace the Use-ITI boolean parameter with a three-state Stim-Mode parameter, allowing either ITI, In-Phase, or Hybrid-ITI modes of operation; (b) for configurations with Stim-Mode set to ITI or In-Phase modes, the behavior is as described in the preferred embodiment; and (c) for configurations with Stim-Mode set to Hybrid-ITI, the Stimulation Timing Policy will treat the ITI (time) parameter as a timeout, after which a stimulation is guaranteed to be played in the event that a slow-wave-up-state is not otherwise detected (and used to trigger sensory stimulation).

In some embodiments, a combination stimulation profile includes a subset of parameters defining behavior within a stimulation block including an in-phase delay and inter-tone interval (ITI) and number to consecutive sensory stimulations to be delivered.

In some embodiments, the combination stimulation profile also includes a subset of parameters defining behavior between stimulation blocks: including a) a time-based inter-block interval (IBI-Time), or amount of time to pause stimulation after the Block-Count parameter is satisfied, before beginning stimulation again; b) a slow-wave-count inter-block interval (IBI-Count), or number of slow-waves to skip after the Block-Count parameter is satisfied, before beginning stimulation again; c) a flag indicating whether the IBI-Time or IBI-Count (IBI-Mode) parameter is to be used on a given night, or within a given sleep cycle, determined by the enclosing application as needed; and/or d) a sync-each-block flag (Sync-Each-Block), indicating whether each block of stimulation should synchronize its first stimulation with the up-state of a slow-wave (after the inter-block interval, IBI, has been satisfied). In some embodiments, the combination stimulation profile also includes a subset of parameters defining behavior that transcends stimulation blocks: a) a Policy delay (Policy-Delay), specifying a duration of time to wait, after detecting suitable stimulation conditions, before beginning stimulation blocks altogether; b) an arousal delay (Arousal-Delay), specifying a duration of time to wait, after detecting arousal conditions, before allowing stimulation blocks to begin, or continue again; and/or c) a sync-first-block flag (Sync-First-Block), indicating whether the very first NREM stimulation block should synchronize its first stimulation with the up-state of the first subsequent slow-wave, independent of the Sync-Each-Block parameter in the previous section.

In some embodiments, the set of parameters provides for a fully specified configuration, which allows all stimulation profiles to be achieved on integrated embedded system 100.

In some embodiments, sleep slow-wave detection subsystem 114 is configured to detect sleep slow waves in the patient based on the brain activity information (from sensor 102) of the patient during the sleep session. Signal analysis unit is not limited to the blocks described above. In some embodiments, sleep slow-wave detection subsystem 114 may be replaced by any logic that estimates (optimal) sleep slow wave or omitted. In some embodiments, sleep slow-wave detection subsystem 114 is configured to use state of the art sleep staging algorithms to automatically detect the sleep stage the subject is currently in. Additionally, in some embodiments, sleep slow-wave detection subsystem 114 is configured to monitor sleep depth and arousals.

In some embodiments, sleep slow-wave detection subsystem 114 and/or stimulation profile detection subsystem 116 are configured to define the stimulation time when sensory stimulation can be delivered to the patient and the determined stimulation profile, respectively. In some embodiments, this information (i.e., the time when sensory stimulation can be delivered to the patient and the determined stimulation profile) is sent to sensory stimulator control subsystem 118.

In some embodiments, sensory stimulator control subsystem 118 is configured to receive information (from sleep slow-wave detection subsystem 114 and/or stimulation profile detection subsystem 116) and to provide input to sensory stimulator 104 based on the received information, the provided input causing sensory stimulator 104 to deliver the sensory stimulation to the patient based on the determined stimulation profile. In some embodiments, the provided input includes starting, continuing/resuming, adjusting or stopping the sensory stimulation. In some embodiments, computer system 106 is configured to adjust, in real-time or near real-time, the stimulation intensity (e.g., volume) of the sensory stimulation to enhance the sleep slow waves without provoking arousals in the patient.

An arousal event may include waking from sleep and/or other arousal events associated with wakefulness of the patient. Responsive to detecting the possible arousal event, sensory stimulator control subsystem 118 may cause sensory stimulator 104 to cease providing sensory stimulation and then determine whether the possible arousal event was a false arousal event. In some embodiments, responsive to determining that the possible arousal event was a false arousal event, sensory stimulator control subsystem 118 may cause sensory stimulator 104 to resume/continue providing sensory stimulation determined based on the recently determined stimulation profile information and the recent brain activity information.

If a possible arousal is detected by system 100 during sensory stimulation, sensory stimulator control subsystem 118 controls sensory stimulator 104 such that the stimulation stops. If an arousal is detected outside the sensory stimulation period, the onset of the stimulation is delayed. If no arousal is detected, then system 100 delivers sensory stimulation based on the recently determined stimulation profile. As described above, responsive to determining that the possible arousal event was a false arousal event, sensory stimulator control subsystem 118 may cause sensory stimulator 104 to resume/continue providing sensory stimulation based on the recently determined stimulation profile.

In some embodiments, the block diagram of elements in this present patent application is shown in FIG. 2. In some embodiments, the top right portion of FIG. 2 shows the basic logic to stop sensory stimulation if the likelihood of disturbing sleep (reflected by the presence of a sleep micro-arousal) increases. In some embodiments, system 100 of the present patent application is configured to stimulate throughout detected deep sleep.

The system of the present patent application is configured to be used with any system that utilizes auditory or other stimulations during deep sleep to enhance sleep restoration. The system of the present patent application supports that system by making it possible to flexibly modulate stimulation timing and grouping. The system of the present patent application is configured to provide multiple stimulation timing strategy options for that system. In some embodiments, that system is configured to support a large variety of stimulation timing strategies/profiles.

In some embodiments, system 100 of the present patent application includes a closed loop control system that is configured both to provide the user/patient with information and to solicit input from the user/patient. For example, system 100 of the present patent application may solicit input from the user/patient such as "what would you like to optimize (e.g., memory consolidation, aldosterone levels, cortisol levels, executive function, verbal fluency) tonight?."

In some embodiments, system 100 may also provide the user/patient with information such as "This is how this system worked for you (or users like you)." In some embodiments, system 100 is configured to be self-optimizing through the means that have been described in detail throughout this application and also through other possible means (e.g., overall sleep architecture/quality, daytime function (e.g., self-report or automatic), or other means to determine an optimal stimulation strategy/profile per-user/patient. Thus, system 100 is configured to self-optimize the stimulation strategy/profile based on two options: 1) user/patient define the cognitive/subjective domain they want to enhance, and/or 2) system 100 detects that sensory stimulation causes positive/adverse effects (e.g., high local delta power increase/tone-related micro-arousals) and defines switching from a continuous fixed-ITI to a block (or continuous) in-phase stimulation strategy.

In some embodiments, some different types of stimulation strategies have differentiated effects on cognitive domains. For instance, the fixed ITI stimulation strategy is relevant for vigilance and executive function, block stimulation strategy is relevant for memory consolidation, and continuous in-phase stimulation strategy is relevant for subjective sleep. In some embodiments, system 100 allows users select the cognitive domain they want to enhance and the system will then select the appropriate stimulation strategy/profile.

In some embodiments, system 100 protects the flexibility of any system that can render any type of stimulation strategy by simply modifying few configuration parameters. In some embodiments, system 100 does not need the prediction aspect because its integrated system targets the slow-wave up-state based on the fact that the second zero-crossing (referred to as positive going zero-crossing in the figures) can be detected and the stimulation can be delayed by a few milliseconds after detection of that event.

Figure 6:
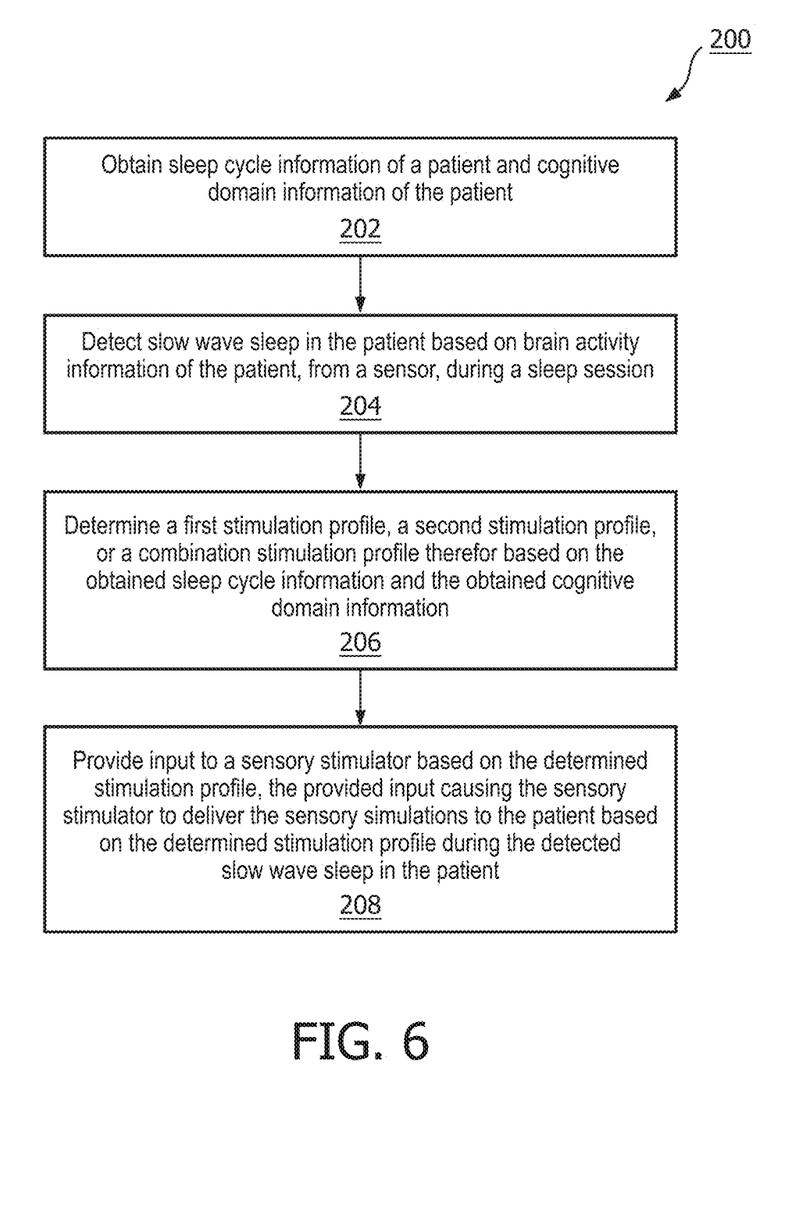
FIG. 6 shows an exemplary method for delivering sensory stimulation in accordance with an embodiment of the present patent application.

Referring to FIG. 6, a method 200 for delivering sensory stimulation is provided. Method 200 is implemented by computer system 106 that comprises one or more physical/hardware processors 108 executing computer program/machine readable instructions that, when executed, perform method 200. In some embodiments, method 200 comprises obtaining sleep cycle information of a patient and cognitive domain information of the patient at procedure 202; detecting slow wave sleep in the patient based on brain activity information of the patient, from a sensor 102, during a sleep session at procedure 204; determining a first stimulation profile, a second stimulation profile, or a combination stimulation profile thereof based on the obtained sleep cycle information and the obtained cognitive domain information at procedure 206; and providing input to a sensory stimulator based on the determined stimulation profile, the provided input causing the sensory stimulator to deliver the sensory simulations to the patient based on the determined stimulation profile during the detected slow wave sleep in the patient at procedure 208.

In some embodiments, a subsystem of system 100 is configured to continuously obtain subsequent brain activity information, and the sleep cycle information. As an example, the subsequent information may comprise additional information corresponding to a subsequent time (after a time corresponding to information that was used to determine the stimulation profile). In some embodiments, a subsystem of system 100 may be configured to control sensory stimulator 104 to adjust the sensory stimulation to the patient in accordance with a recursively refined profile (e.g., refined through recursive application of profile refinement algorithms) based on previously collected or subsequent information.

In some embodiments, system 100 is configured to obtain input parameters from the patient. In some embodiments, these input parameters may include age (e.g., by means of a one-time questionnaire where the user could input his/her date of birth), mental states (e.g., subjective impression of current/past level of stress), or the result of daytime activity tracking (e.g., the amount and intensity of physical activity).

In some embodiments, the input parameters are input by the patient (or caregiver) into computer system 106 using user interface 160. In some embodiments, computer system 106 may include patient input parameter information subsystem for further processing this information. In some embodiments, system 100 is configured to receive patient input parameter information to determine the stimulation profile using the patient input parameter information. In some embodiments, system 100 is configured to adapt some of its system parameters based on the obtain input parameters from the patient.

In some embodiments, the various computers and subsystems illustrated in FIG. 3 may comprise one or more computing devices that are programmed to perform the functions described herein. The computing devices may include one or more electronic storages (e.g., database 132, or other electronic storages), one or more physical processors programmed with one or more computer program instructions, and/or other components. The computing devices may include communication lines or ports to enable the exchange of information with a network (e.g., network 150) or other computing platforms via wired or wireless techniques (e.g., Ethernet, fiber optics, coaxial cable, WiFi, Bluetooth, near field communication, or other communication technologies). The computing devices may include a plurality of hardware, software, and/or firmware components operating together to provide the functionality attributed herein to the servers. For example, the computing devices may be implemented by a cloud of computing platforms operating together as the computing devices.

The electronic storages may comprise non-transitory storage media that electronically stores information. The electronic storage media of the electronic storages may include one or both of system storage that is provided integrally (e.g., substantially non-removable) with the servers or removable storage that is removably connectable to the servers via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information received from the servers, information received from client computing platforms, or other information that enables the servers to function as described herein.

The processors may be programmed to provide information processing capabilities in the servers. As such, the processors may include one or more of a digital processor, an analog processor, or a digital circuit designed to process information, an analog circuit designed to process information, a state machine, and/or other mechanisms for electronically processing information. In some embodiments, the processors may include a plurality of processing units. These processing units may be physically located within the same device, or the processors may represent processing functionality of a plurality of devices operating in coordination. The processors may be programmed to execute computer program instructions to perform functions described herein of subsystems 112-118 or other subsystems. The processors may be programmed to execute computer program instructions by software; hardware; firmware; some combination of software, hardware, or firmware; and/or other mechanisms for configuring processing capabilities on the processors. In some embodiments, hardware processors may be interchangeably referred to as physical processors. In some embodiments, machine readable instructions may be interchangeably referred to as computer program instructions.

It should be appreciated that the description of the functionality provided by the different subsystems 112-118 described herein is for illustrative purposes, and is not intended to be limiting, as any of subsystems 112-118 may provide more or less functionality than is described. For example, one or more of subsystems 112-118 may be eliminated, and some or all of its functionality may be provided by other ones of subsystems 112-118. As another example, additional subsystems may be programmed to perform some or all of the functionality attributed herein to one of subsystems 112-118.

It should be appreciated that the different subsystems 112-118 performing the operations illustrated in FIG. 3 may reside in a system with sensor 102 and sensory stimulator 104. In some embodiments, the different subsystems 112-118 performing the operations illustrated in FIG. 3 may reside in an independent monitoring device.

In some embodiments, computer system 106 and/or physical processors/server 108 are included in a smartphone associated with the patient and/or other computing devices. In some embodiments, computer system 106 and/or physical processors/server 108 are included in a tablet computer, a laptop computer, a desktop computer, a server computer, and/or other computing devices. In some embodiments, the smartphone comprises an input configured to receive the information in the output signals generated by sensor 102 and/or other information. The input device may be and/or include a microphone included in the smartphone, a USB input device, an Apple Lightning type connector (which can also provide power), a combined microphone/earphones jack, and/or other devices. In some embodiments, converter devices are configured to convert the output signals, and/or the information in the output signals from sensor 102 for transmission to, and receipt by, the smartphone input device. In some embodiments, computer system 106 and/or physical processors/server 108 are configured such that subsystems 112-118, and/or other subsystems form an electronic application (an "app") running on computer system 106 and/or physical processors/server 108. In some embodiments, the app (as described above related to subsystems 112-118, and/or other subsystems) reads the transformed signal from converter and transmitter devices, converts it back to an EEG signal (if necessary), and analyzes the signal to determine the information described above.

In some embodiments, as shown in FIGS. 3 and 4, system 100 may include user interface 106 be configured to provide an interface between system 100 and a user (e.g., a patient or a caregiver, etc.) through which the user can provide information to and receive information from system 100. This enables data, results, and/or instructions and any other communicable items, collectively referred to as "information," to be communicated between the user and system 100. Examples of interface devices suitable for inclusion in user interface include a keypad, buttons, switches, a keyboard, knobs, levers, a display screen, a touch screen, speakers, a microphone, an indicator light, an audible alarm, and a printer. In some embodiments, information may be provided to the patient by the user interface in the form of auditory signals, visual signals, tactile signals, and/or other sensory signals. It is to be understood that other communication techniques, either hard-wired or wireless, are also contemplated herein as the user interface. For example, in some embodiments, the user interface may be integrated with a removable storage interface provided by electronic storage 132. In this example, information is loaded into system 100 from removable storage (e.g., a smart card, a flash drive, a removable disk, etc.) that enables the user(s) to customize system 100. Other exemplary input devices and techniques adapted for use with system 100 as user interface include, but are not limited to, an RS-232 port, RF link, an IR link, modem (telephone, cable, Ethernet, internet or other). In short, any technique for communicating information with system 100 is contemplated as the user interface.

In some embodiments, system 100 may also include a communication interface that is configured to send input/control signals to sensory stimulator 104 based on the determined parasympathetic nervous system information through an appropriate wireless communication method (e.g., Wi-Fi, Bluetooth, internet, etc.). In some embodiments, system 100 may include a recursive tuning subsystem that is configured to recursively tune its intelligent decision making subsystem using available data or information to provide better overall adjustment of sensory stimulator 104 and/or better overall control of sensory stimulator 104. In some embodiments, intelligent decision making subsystem, communication interface and recursive tuning subsystem may be part of computer system 106 (comprising server 108).

In some embodiments, system 100 is used with any sleep devices/systems, any sleep portfolios, any sleep solutions that are known to one skilled in the art. In some embodiments, system 100 is used in a clinical setting sleep devices/systems. In some embodiments, system 100 is used in a home setting sleep devices/systems. In some embodiments, a mobile application can be part of the health suite digital platform.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. A system for delivering sensory stimulation to a patient, comprising:
    a sensor configured to measure brain activity information of the patient during a sleep session;
    a sensory stimulator configured to deliver sensory simulations to the patient during the sleep session; and
    a computer system that comprises one or more physical processors (108) operatively connected with the sensor and the sensory stimulator, the one or more physical processors being programmed with computer program instructions which, when executed cause the computer system to:
    obtain sleep cycle information of the patient and cognitive domain information of the patient;
    detect slow wave sleep in the patient based on the brain activity information of the patient during the sleep session from the sensor;
    determine a first stimulation profile, a second stimulation profile, and a combination stimulation profile thereof based on the obtained sleep cycle information and the obtained cognitive domain information; and
    provide input to the sensory stimulator based on the determined stimulation profiles, the provided input causing the sensory stimulator to deliver the sensory simulations to the patient based on the determined stimulation profiles during the detected slow wave sleep in the patient.

2. The system of claim 1, wherein each of the first, second and combination stimulation profiles include information that is selected from the group consisting of simulation timing when the sensory stimulation is delivered to the patient, duration of a sensory stimulation block, number of tones in the sensory stimulation block, in-phase time delay from a positive going zero-crossing, time based inter-block interval (IBI), an inter-tone interval (ITI), number of sleep slow waves to skip between sensory stimulation blocks, a duration to wait after detecting suitable stimulation conditions and before beginning the sensory stimulation blocks, a duration to wait after detecting arousal conditions and before beginning the sensory stimulation blocks, whether to synchronize a sensory stimulation block its first sensory stimulation with an up-state of a first subsequent slow-wave after the duration of the inter-block interval (IBI) is satisfied, and a time delay after the slow wave sleep is detected and before beginning the sensory stimulation blocks.

3. The system of claim 1, wherein the cognitive domain information is selected from the group consisting of verbal memory, non-verbal memory, memory consolidation, endocrine activity level, motors skills, executive function, visual spatial skills, verbal fluency, attention, and information processing; and
    wherein the sleep cycle information is selected from the group consisting of time from sleep onset, biological signals, sleep patterns, sleep phases, sleep cycles, and/or a measure of quality of a user's sleep.

4. The system of claim 1, wherein the sensory stimulation is selected from the group consisting of olfactory stimulation, auditory stimulation, visual stimulation, touch stimulation, taste stimulation, haptic stimulation, peripheral stimulation, magnetic stimulation and electrical stimulation.

5. The system of claim 1, the computer system is configured to determine an arousal based on the brain activity information of the patient, and provide input to the sensory stimulator based on the determined arousal, the provided input causing the sensory stimulator to stop or delay delivering the sensory stimulation to the patient based on the determined arousal.

6. A method for delivering sensory stimulation, the method being implemented by a computer system that comprises one or more physical processors executing computer program instructions that, when executed, perform the method, the method comprising:
   obtaining sleep cycle information of a patient and cognitive domain information of the patient;
   detect slow wave sleep in the patient based on brain activity information of the patient during the sleep session from a sensor;
   determining, using the computer system, a first stimulation profile, a second stimulation profile, and a combination stimulation profile thereof based on the obtained sleep cycle information and the obtained cognitive domain information; and
   providing, using the computer system, input to a sensory stimulator based on the determined stimulation profiles, the provided input causing the sensory stimulator to deliver the sensory simulations to the patient based on the determined stimulation profiles during the detected slow wave sleep in the patient.

7. The method of claim 6, wherein each of the first, second and combination stimulation profiles include information that is selected from the group consisting of simulation timing when the sensory stimulation is delivered to the patient, duration of a sensory stimulation block, number of tones in the sensory stimulation block, in-phase time delay from a positive going zero-crossing, time based inter-block interval (IBI), an inter-tone interval (ITT), number of sleep slow waves to skip between sensory stimulation blocks, a duration to wait after detecting suitable stimulation conditions and before beginning the sensory stimulation blocks, a duration to wait after detecting arousal conditions and before beginning the sensory stimulation blocks, whether to synchronize a sensory stimulation block its first sensory stimulation with an up-state of a first subsequent slow- wave after the duration of the inter-block interval) is satisfied, and a time delay after the slow wave sleep is detected and before beginning the sensory stimulation blocks.

8. The method of claim 6, wherein the cognitive domain information is selected from the group consisting of verbal memory, non-verbal memory, memory consolidation, endocrine activity level, motors skills, executive function, visual spatial skills, verbal fluency, attention, and information processing; and
   wherein the sleep cycle information is selected from the group consisting of time from sleep onset, biological signals, sleep patterns, sleep phases, sleep cycles, and/or a measure of quality of a user's sleep.

9. The method of claim 6, wherein the sensory stimulation is selected from the group consisting of olfactory stimulation, auditory stimulation, visual stimulation, touch stimulation, taste stimulation, haptic stimulation, peripheral stimulation, magnetic stimulation and electrical stimulation.

10. The method of claim 6, wherein the method further comprises determining, using the computer system, an arousal based on the brain activity information of the patient, and providing, using the computer system, input to the sensory stimulator based on the determined arousal, the provided input causing the sensory stimulator to stop or delay delivering the sensory stimulation to the patient based on the determined arousal.

\* \* \* \* \*